United States Patent [19]

Hofer et al.

[11] 4,227,918

[45] Oct. 14, 1980

[54] NOVEL HALOGENOETHYL SULPHONES AND THEIR USE AS PLANT GROWTH REGULATORS

[75] Inventors: Wolfgang Hofer, Wuppertal; Klaus Lürssen, Bergisch-Gladbach, both of Fed. Rep. of Germany

[73] Assignee: Bayer Aktiengesellschaft, Leverkusen, Fed. Rep. of Germany

[21] Appl. No.: 965,966

[22] Filed: Dec. 4, 1978

Related U.S. Application Data

[62] Division of Ser. No. 856,056, Nov. 30, 1978.

[30] Foreign Application Priority Data

Dec. 17, 1976 [DE] Fed. Rep. of Germany ....... 2657380

[51] Int. Cl.² .............................................. A01N 9/14
[52] U.S. Cl. ......................................... 71/103; 568/32
[58] Field of Search ................... 260/607 AL; 71/103

[56] References Cited

U.S. PATENT DOCUMENTS

| | | | |
|---|---|---|---|
| 3,094,455 | 6/1963 | Allen et al. ............... 260/607 AL X |
| 3,509,218 | 4/1970 | Allen et al. ................... 260/607 AL |
| 3,556,714 | 1/1971 | Tesoro .......................... 260/607 AL |
| 3,876,678 | 4/1975 | Pilgram et al. .................... 71/103 X |
| 3,885,951 | 5/1975 | Hofer et al. ............................. 71/103 |
| 4,057,418 | 11/1977 | Hofer et al. ............................. 71/103 |
| 4,087,271 | 5/1978 | Rheinecker ........................ 71/103 X |
| 4,098,599 | 7/1978 | Arneklev ............................ 71/103 X |
| 4,134,752 | 1/1979 | Pilgram et al. ......................... 71/103 |

OTHER PUBLICATIONS

C.A., 61 (1964), 8493d (Tesoro et al.).

*Primary Examiner*—Joseph P. Brust
*Attorney, Agent, or Firm*—Sprung, Felfe, Horn, Lynch & Kramer

[57] ABSTRACT

A halogenoethyl sulphone of the formula

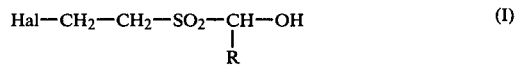

wherein
 Hal represents halogen; and
 R represents hydrogen or an alkyl group of 1 to 6 carbon atoms, the use of such halogenoethyl sulphone as plant growth regulants and a process for regulating the growth of a crop by applying to the crop or a habitat thereof a composition comprising such halogenoethyl sulphone.

8 Claims, No Drawings

NOVEL HALOGENOETHYL SULPHONES AND THEIR USE AS PLANT GROWTH REGULATORS

This is a division of application Ser. No. 856,056 filed Nov. 30, 1977.

The present invention relates to certain new halogenoethyl sulphones, to a process for their preparation and to their use as active compounds for regulating plant growth.

It has already been disclosed in Published Netherlands patent specification No. 6,802,633 and Belgian patent specification No. 816,435 that 2-chloroethanephosphonic acid and the methyl sulphate of 1-methyl-sulphonium-4-thia-cyclohexane display plant growth regulating properties. However, the effectiveness of these substances is not always entirely satisfactory, especially at low concentrations and/or low application rates.

The present invention now provides, as new compounds, the halogenoethyl sulphones of the general formula

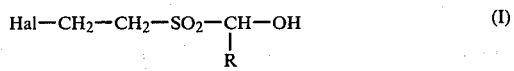

in which
  Hal represents halogen and
  R represents hydrogen or alkyl with 1 to 6 carbon atoms.

The compounds of the formula (I) display powerful plant growth-regulating properties.

Preferably, Hal represents chlorine or bromine and R represents hydrogen or straight-chain or branched alkyl with 1 to 4 carbon atoms (especially methyl, ethyl, n-propyl or iso-propyl).

The invention also provides a process for the preparation of halogenoethyl sulphone of the formula (I), in which a halogenoethane-sulphinic acid of the general formula

in which
  Hal has the meaning stated above,
is reacted with an aldehyde of the general formula

in which
  R has the meaning stated above,
optionally in the presence of a solvent or diluent.

Surprisingly, the halogenoethyl sulphones according to the invention display a considerably greater plant growth-regulating action than 2-chloroethanephosphonic acid, which is known from the state of the art, and the methyl sulphate of 1-methylsulphonium-4-thiacyclohexane, which is also known, these two compounds being effective active compounds having the same type of action. The substances according to the invention thus represent a valuable enrichment of the art.

If 2-chloroethane-sulphinic acid and acetaldehyde are used as the starting materials, the course of the reaction can be represented by the following equation:

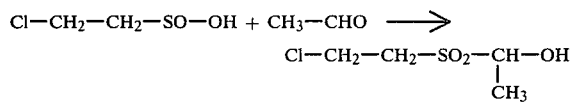

The halogenoethane-sulphinic acids of the formula (II) which can be used according to the invention are already known or can be prepared by generally customary processes see German Offenlegungsschrift No. 2,110,773.

Examples which may be mentioned of the compounds of the formula (II) are: 2-chloroethane-sulphinic acid and 2-bromoethane-sulphinic acid.

The compounds of the formula (III) which can be used according to the invention are known and can be prepared by generally customary methods, even on an industrial scale.

Examples which may be mentioned of the compounds of the formula (III) are: formaldehyde, acetaldehyde, propionaldehyde, butyraldehyde and isobutyraldehyde.

The process for the preparation of the compounds according to the invention can be carried out in the presence of a suitable solvent or diluent. Virtually any of the inert organic solvents can be used, especially aliphatic and aromatic, optionally chlorinated, hydrocarbons, such as benzene, toluene, xylene, benzene, methylene chloride, chloroform, carbon tetrachloride and chlorobenzene, and ethers, such as, for example, diethyl ether, dibutyl ether and dioxan. Finally, the reaction according to the invention can particularly preferentially be carried ou in the aqueous phase.

The reaction temperature can be varied within a relatively wide range. In general, the reaction is carried out at from 10° C. to 60° C. and preferably at from 15° C. to 30° C.

The reaction according to the invention is generally carried out at normal pressure.

When carrying out the process according to the invention in order to prepare the compounds of the formula (I), the starting materials are generally employed in equimolar amounts. An excess of one or the other component brings no substantial advantage. If a water-containing aldehyde is used in the reaction according to the invention or if the reaction is carried out in the aqueous phase, the compounds of the formula (I) are generally isolated by distilling off the water under reduced pressure after the reaction has ended, taking up the residue in an organic solvent, for example methylene chloride, drying the organic phase and filtering and then stripping off the solvent. If anhydrous aldehydes and organic solvents are used in the reaction according to the invention, the compounds of the formula (I) are generally isolated by distilling off the solvent under reduced pressure after the reaction has ended and, if necessary, subjecting the residue to an additional purification.

The compounds of the formula (I), which can be prepared according to the invention, are obtained, after working up, in the form of oils which frequently cannot be distilled without decomposition. In these cases, the purification can be carried out by freeing the crude products from the final volatile constituents by so-called "slight distillation", that is to say by prolonged heating under reduced pressure to moderately elevated temperatures. The refractive index is used for characterisation.

Examples which may be mentioned individually of the halogenoethyl sulphones according to the invention are: 2-chloroethyl-hydroxymethyl sulphone, 2-bromoethyl-hydroxymethyl sulphone, 2-chloroethyl-1-hydroxyethyl sulphone, 2-bromoethyl-1-hydroxyethyl sulphone, 2-chloroethyl-1-hydroxy-n-propyl sulphone, 2-bromoethyl-1-hydroxy-n-propyl sulphone, 2-chloroethyl-1-hydroxy-n-butyl sulphone, 2-bromoethyl-1-hydroxy-n-butyl sulphone, 2-chloroethyl-1-hydroxy-isobutylsulphone and 2-bromoethyl-1-hydroxy-isobutyl sulphone.

The compounds according to the present invention engage in the metabolism of plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds or at verges. The inhibition of growth of herbaceous and woody plants at verges and in the vicinity of overland pipelines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which can counteract lodging.

In the case of many crop plants, inhibition of the vegetative growth permits denser planting of the crop, so that a greater yield per area of ground can be achieved.

A further mechanism of increasing the yield by means of growth inhibitors is based on the fact that the nutrients benefit blossoming and fruit formation to a greater extent, whilst vegetative growth is restricted.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals.

Parthenocarpous fruit can be formed under the influence of growth regulators. Furthermore, the gender of the flowers can be influenced.

Using growth regulators it is also possible favourably to influence the production or the flux of secondary plant materials. The stimulation of latex flow in rubber trees may be mentioned as an example.

During the growth of the plant, lateral branching can also be increased, by using growth regulators, through chemical breaking of the apical dominance. There is interest in this, for example, in the case of plant propagation by cuttings. However, it is also possible to inhibit the growth of side shoots, for example to prevent the formation of side shoots in tobacco plants after decapitation and thus to promote leaf growth.

The amount of leaf on plants can be controlled, under the influence of growth regulators, so that defoliation of the plants at a desired point in time is achieved. Such defoliation is of interest to facilitate mechanical harvesting, for example of grapes or cotton, or to lower the transpiration at a point in time at which the plant is to be transplanted.

Premature shedding of fruit can be prevented by the use of growth regulators. However, it is also possible to promote the shedding of fruit—for example in the case of table fruit—in the sense of a chemical thinning out, up to a certain degree. Growth regulators can also be used to reduce the force required to detach the fruit from crop plants at harvest time so as to permit mechanical harvesting of the plants or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators it is also possible to influence the latent period of seeds or buds of plants, that is to say the endogenic annual rhythm, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds according to the instant invention can be utilized, if desired, in the form of the usual formulation or compositions with conventional inert (i.e., plant compatible) diluents or extenders, i.e. diluents, carriers or extenders of the type usable in conventional plant growth formulations or compositions, e.g. conventional diespersible carrier vehicles such as gases, solutions, emulsions, wettable powders, suspensions, powder dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons (dichlorodifluoromethane or trichlorofluoromethane) as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylene, etc.), alcohols (e.g. methanol, ethanol, propanol, butanol, glycol, etc.), as well as ethers and esters thereof (e.g. glycol monomethyl ether, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as high-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl aryl-polyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially other plant protection agents, such as other insecticides, acaricides, fungicides, bactericides, rodenticides and fertilizers herbicides, plant growth regulators, if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between 0.0000001–100, preferably 0.01–10% by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of active compound which is effective for the purpose in question and which is generally between about 0.0001–95%, and preferably 0.01–95%, by weight of the mixture, preferably 0.1 to 95%, more preferably 0.5 to 90 weight percent.

The amount of active compound used can vary within a fairly wide range. It depends essentially on the nature of the desired effect. In general, the amounts used are from 0.01 to 50 kg, especially 0.05 to 10 kg of active compound per hectare.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

The plant-growth-regulating activity of the compounds of this invention is illustrated by the following biotest Examples.

In these Examples, the compounds according to the present invention are each identified by the number (given in brackets) of the corresponding preparative Example, which will be found later in this specification.

The known comparison compounds are identified as follows:

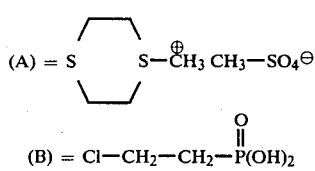

(B) = Cl—CH$_2$—CH$_2$—P(OH)$_2$ with =O

EXAMPLE A

Influence on growth/beans

Solvent: 10 parts by weight of methanol
Emulsifier: 2 parts by weight of polyoxyethylene sorbitan monolaurate To prepare a suitable preparation of active compound, 1 part by weight of active compound was mixed with the stated amounts of solvent and emulsifier and the mixture was made up to the desired concentration with water.

Young bean plants, in the stage in which the juvenile leaves had unfolded completely, were sprayed with the preparations of active compound until dripping wet. After 3 weeks, the additional growth was measured and the influence on growth in % of the additional growth of the control plants was calculated. 0% denotes a growth corresponding to that of the untreated control plants. Positive values indicated a promotion of growth in comparison to the control plants whilst negative values correspondingly indicated an inhibition of growth.

The active compounds, active compound concentrations and results can be seen from the table which follows:

TABLE A

| Active compound | Active compound concentration in % | Influence on growth in % |
|---|---|---|
| (2) | 0.05 | +70 |
| (1) | 0.05 | +55 |
| (A) | 0.05 | +15 |
| Control | — | 0 |

EXAMPLE B

Influence on growth/cotton

Solvent: 10 parts by weight of methanol
Emulsifier: 2 parts by weight of polyoxyethylene sorbitan monolaurate To prepare a suitable preparation of active compound, 1 part by weight of active compound was mixed with the stated amounts of solvent and emulsifier and the mixture was made up to the desired concentration with water.

Yound cotton plants in the 4-leaf stage were sprayed with the preparation of active compound until dripping wet. After 3 weeks, the additional growth was measured and the influence on growth was calculated in % of the additional growth of the control plants. 0% denotes a growth which corresponded to that of the control plants. Positive values characterised a promotion of growth in comparison to the control plants whilst negative values correspondingly indicated an inhibition of growth.

The active compounds, active compound concentrations and results can be seen from the table which follows.

TABLE B

| Active compound | Active compound concentration in % | Influence on growth in % |
|---|---|---|
| (3) | 0.05 | +10 |
| Control | — | 0 |

EXAMPLE C

Acceleration of ripening/bananas

Solvent: 10 parts by weight of methanol
Emulsifier: 2 parts by weight of polyoxyethylene sorbitan monolaurate To prepare a suitable preparation of active compound, 1 part by weight of active compound was mixed with the stated amounts of solvent and emulsifier and the mixture was made up to the desired concentration with water.

In each case 3 unripe bananas were sprayed with 20 ml of the active compound preparation. The acceleration of ripening in days compared to untreated control fruits was determined.

The active compounds, active compound concentration and results can be seen from the table which follows:

TABLE C

| Active compound | Active compound concentration in % | Acceleration of ripening in days |
|---|---|---|
| Control | — | 0 |
| (2) | 0.2 | 3 |
| (1) | 0.2 | 3 |

EXAMPLE D

Inhibition of growth/tomatoes

Solvent: 10 parts by weight of methanol
Emulsifier: 2 parts by weight of polyoxyethylene sorbitan monolaurate To prepare a suitable preparation of active compound, 1 part by weight of active compound was mixed with the stated amounts of solvent and emulsifier and the mixture was made up to the desired concentration with water.

Tomato plants which were about 30 cm high were sprayed with the active compound preparations until dripping wet. After 10 days, the additional growth was measured and the inhibition of growth in % of the additional growth of the control plants was calculated. 100% meant that growth had stopped and 0% denoted a growth corresponding to that of the control plants.

The active compounds, active compound concentrations and results can be seen from the table which follows:

TABLE D

| Active compound | Active compound concentration in % | Inhibition of growth in % |
|---|---|---|
| Control | — | 0 |
| (2) | 0.2 | 50 |
|  | 0.1 | 40 |
|  | 0.05 | 40 |
| (1) | 0.2 | 45 |

TABLE D-continued

| Active compound | Active compound concentration in % | Inhibition of growth in % |
|---|---|---|
| | 0.1 | 35 |
| | 0.05 | 35 |

EXAMPLE E

Inhibition of growth/barley

Solvent: 10 parts by weight of methanol
Emulsifier: 2 parts by weight of polyoxyethylene sorbitan monolaurate To prepare a suitable preparation of active compound, 1 parts by weight of active compound was mixed with the stated amount of solvent and emulsifier and the mixture was made up to the desired concentration with water.

Young barley plants, in the 2-leaf stage, were sprayed with the preparation of active compound until dripping wet. After the untreated control plants had reached a growth height of about 60 cm, the additional growth of all the plants was measured and the inhibition of growth in % of the additional growth of the control plants was calculated. 100% meant that growth had stopped and 0% denoted a growth corresponding to that of the untreated control plants.

The active compounds, concentrations of the active compounds and results can be seen from the table which follows.

TABLE D

| Active compound | Active compound concentration in % | Inhibition of growth in % |
|---|---|---|
| Control | — | 0 |
| (1) | 0.1 | 15 |
| (B) | 0.05 | 0 |

PREPARATIVE EXAMPLES

Example 1:

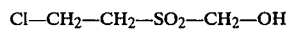 (1)

35 g (0.27 mol) of 2-chloroethane-sulphinic acid were added dropwise at room temperature to 27 g (0.27 mol) of a 30% strength aqueous formaldehyde solution. The reaction mixture was stirred for a further hour at room temperature, the water was then distilled off in vacuo at a bath temperature of 40° C. and the residue was taken up in methylene chloride. The reaction solution was freed from residual water by introducing sodium sulphate into the solution. After filtering off the sodium sulphate and stripping off the solvent, 39 g (90.5% of theory) of 2-chloroethyl hydroxymethyl sulphone remained as a colourless oil having a refractive index $n_D^{22}$ of 1.4978. The structure was demonstrated by NMR and IR spectra.

The compounds mentioned in the Examples which follow were prepared analogously:

EXAMPLE 2

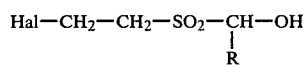

Yield: 70% of theory
Refractive index:
$n_D^{20} = 1.4538$

EXAMPLE 3

Cl—CH$_2$—CH$_2$—SO$_2$—CH—OH
        |
(3)     CH$_2$—CH$_2$—CH$_3$

Yield: 72% of theory
Refractive index:
$n_D^{20} = 1.5437$

What we claim is:
1. A method of regulating the growth of plants which comprises applying to the plant or to a habitat thereof, a plant growth regulating amount of a compound having the formula

$$\text{Hal}-CH_2-CH_2-SO_2-\underset{R}{\underset{|}{CH}}-OH$$

wherein
Hal represents bromine or chlorine, and
R represents hydrogen or alkyl with 1 to 4 carbon atoms.

2. A method according to claim 1 wherein said compound is applied to an area of plant cultivation in an amount of 0.01 to 55 kg per hectare.

3. A method according to claim 2 wherein said compound is applied to an area of plant cultivation in an amount of 0.05 to 10 kg per hectare.

4. A method according to claim 1 wherein said plants comprise beans.

5. A method according to claim 1 wherein said plants comprise cotton.

6. A method according to claim 1 wherein said plants comprise banana plants.

7. A method according to claim 1 wherein said plants comprise tomato plants.

8. A method according to claim 1 wherein said plants comprise barley.

* * * * *

UNITED STATES PATENT AND TRADEMARK OFFICE
CERTIFICATE OF CORRECTION

PATENT NO. : 4,227,918
DATED : October 14, 1980
INVENTOR(S) : Wolfgang Hofer et al.

It is certified that error appears in the above—identified patent and that said Letters Patent is hereby corrected as shown below:

Column 2, line 29, "benzene" (second occurrence) should read -- benzine --.

Column 2, line 34, "ou" should read -- out --.

Column 5, line 37, "chloroethylene" should read -- chloroethylenes -- .

Column 7, line 59, "Yound" should read -- Young --.

Signed and Sealed this

Sixth Day of January 1981

[SEAL]

Attest:

SIDNEY A. DIAMOND

Attesting Officer    Commissioner of Patents and Trademarks